United States Patent [19]

Bringhurst et al.

[11] Plant 4,507

[45] Mar. 4, 1980

[54] CN7 STRAWBERRY PLANT

[75] Inventors: Royce S. Bringhurst, Davis; Victor Voth, Santa Ana, both of Calif.

[73] Assignee: The Regents of the University of California, Berkeley, Calif.

[21] Appl. No.: 954,005

[22] Filed: Oct. 23, 1978

[51] Int. Cl.[2] ..... A01H 5/03
[52] U.S. Cl. ..... Plt./49
[58] Field of Search ..... Plt./48–49

*Primary Examiner*—Robert E. Bagwill

[57] ABSTRACT

A new and distinct variety of strawberry plant of a short-day type characterized by its ability after summer planting in South Coastal California to produce fruit during November, December and January when California fruit is unavailable from other short-day cultivars and its ability after winter and spring plantings in Central Coastal California to produce spring and summer fruit without plant storage. The variety is also characterized by vigorous growth, runner prolificacy, fruit which is round conic and glossy in finish, and which has outstanding fruit flavor and good shipping quality.

3 Drawing Figures

This invention relates to a new and distinctive day-neutral type strawberry cultivar designated as "CN7" which is the result of a cross between Cal 66s96-101 (not patented) and Cal 65.65-601 (not patented), a second generation backcross derivative from *Fragaria virginiana glauca* from Utah.

CN7 first fruited at the Wolfskill Experimental Orchards of the University of California near Davis in 1970 where it was selected in 1971 and designated originally as Cal 69.141-101.

CN7 has since been tested with varying results and asexually reproduced by runners at various University of California Field Stations and facilities and has also been favorably tested in a limited way in representative growers' fields under strict control. Meristem originated virus negative stock for propogation has been developed by the University of California.

FIG. 1 of the accompanying photographic color reproductions shows typical growth, flowering and fruiting characteristics.

Figure 1:
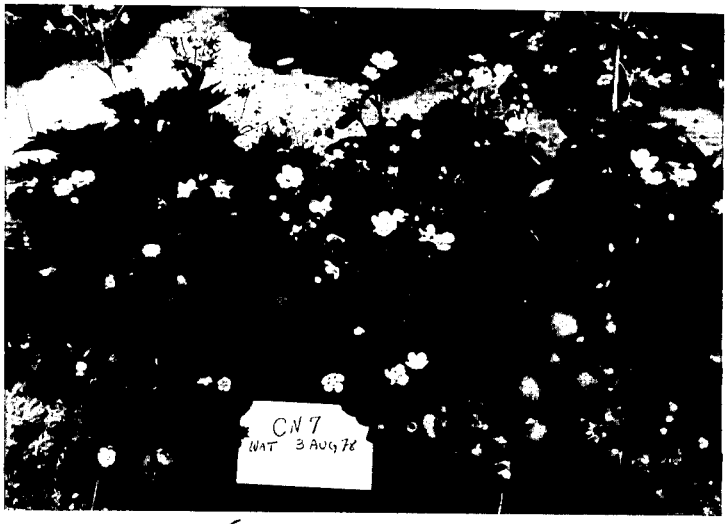
Figure 2:
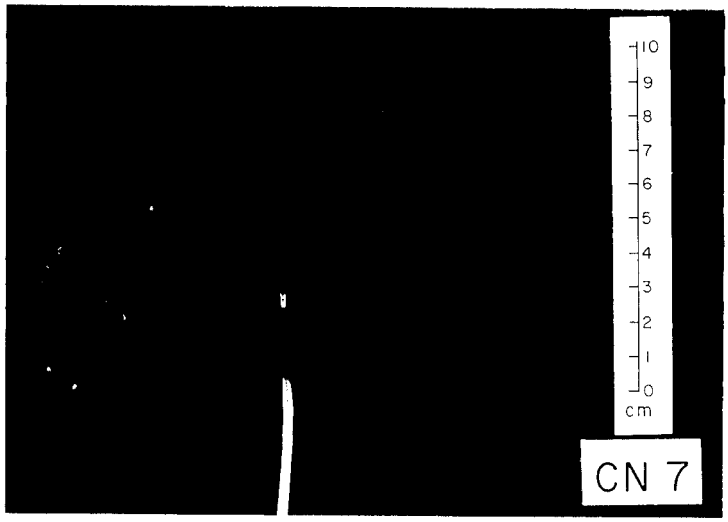
FIG. 2 shows a typical mid-summer mature leaf from a spring planted plant.
Figure 3:
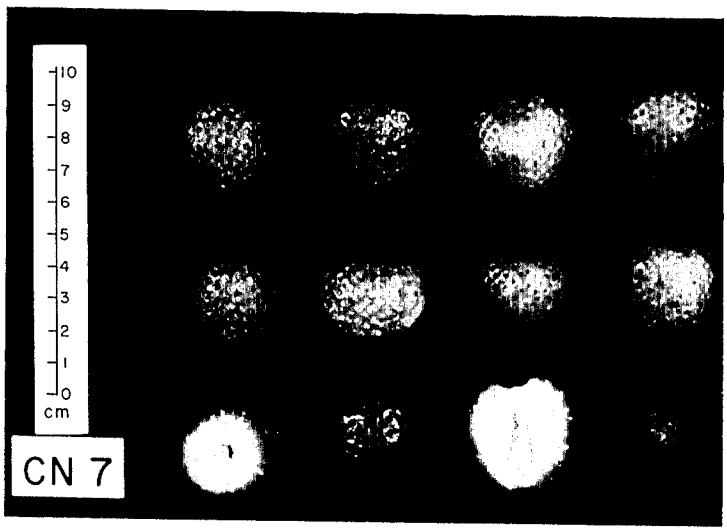
FIG. 3 shows representative mid-season fruit of CN7 with longitudinal and cross section views.

CN7 has performed well in winter fruiting experiments with summer planted plants in south coastal California and in spring to summer fruiting experiments in winter and spring plantings in Central Coastal California. In Southern California CN7 can thus be programmed to produce fruit approximately 3 months after planting during November, December and January, months during which California fruit is not available from the standard short-day cultivars such as "Tioga" (not patented) and "Tufts" (U.S. Plant Pat. No. 3,561). Using the same 3 month rule, CN7 can be programmed to produce spring or summer fruit beginning approximately 3 months after planting with or without plant storage and continuing on a cyclic basis throughout the summer and fall.

The distinctive characteristics of this new strawberry cultivar described below were observed upon its discovery and/or through the test period.

DESCRIPTION

*Plants and foliage.*—CN7 plants are erect in growth habit somewhat similar to "Aiko" (U.S. Plant Pat. No. 3,981); small in size, smaller even than those of "Aiko".

Bract leaves do not occur normally on the petioles of CN7 in contrast to the important California short-day cultivars. Leaflets of CN7 are even smaller than those of the smallest leaved important California short-day cultivar "Aiko" by about 14%. CN7 leaves are about the same color as those of "Tioga", i.e., 2.5 GY 4/3 vs. 2.5 GY 5/7, respectively (Munsell Color System — Nickerson Color Fan). The leaflets have fewer leaf serrations than those of "Aiko" and "Tioga" (av of ±8 vs. ±10/half blade, respectively) and much less than "Tufts" (±12) as averaged over the half blades of the 3 leaflets on midseason mature leaves at Watsonville. The plants are vigorous and CN7 is a prolific runner maker in the nursery. Runner production in the fruiting bed also occurs at variable rates and runner plants always flower within a reasonable period of time whether rooted or not. CN7 differ from other so called "everbearing" types in that CN7 has a very low chilling requirement and consequently will fruit during the winter under adequate temperature conditions.

*Isozymes in leaf extracts.*—Phosphoglucose isomerase (PGI): CN7 gave a single band pattern identical to that of "Tioga", 35/35 35/35 35/35 35/35 mm, distinctive from the slow 3 banded pattern of "Tufts" and the 5 banded pattern of "Aiko" (Scandalios, 1969, Biochem. Genet. 3:37–79).

*Flowering and flowers.*—CN7 is a new type of cultivar in that with minimum conditioning it will flower and fruit anytime, effectively independent of day length. The inflorescences are long, tending almost to an indeterminate growth habit. The flowers are highly self fertile with ample pollen throughout the season.

*Fruit and fruiting.*—CN7 has round conic fruits, generally smooth and solid throughout. The fruit skin color is very similar to that of "Tioga" about 7.5 R 4/11 vs. 7.5 R 4.5/13, respectively (ibid). The finish is glossy and the flesh color is almost the same as the skin ranging to lighter around the core. The achenes are generally flush with the surface similar to those of "Tioga". The fruit is slightly less firm and less durable than that of "Aiko", "Tioga" and "Tufts" giving penetrometer readings of about ±6 vs. ±6.7 for the three cultivars at Watsonville. The average fruit size is smaller than that of "Aiko" or "Tioga" and much smaller than "Tufts", typically about ±15 g/fr vs. ±18, ±18 and ±21, respectively at Watsonville.

*Fruit quality.*—Ascorbic acid: CN7 has averaged ±59 mg/100 g of fresh fruit, much greater than "Tioga", (±40), "Tufts" (±45) and about the same as "Aiko" (±60) as tested by the method of Loeffler and Ponting. 1942 J. Ind. and Eng. Chem. 14:846. Soluble solids; CN7 averaged ±8.0, not significantly different from "Aiko", "Tioga" or "Tufts" according to our test of mid-summer Watsonville fruit. The flavor of CN7 is equal to or better than that of the important California short-day cultivars in our opinion. Some judge it considerably better. CN7 is adequate for shipping if it is picked and packed carefully but only when the fruit size is largest. It may be useful for processing and should be tested for home garden use, where it might be of greatest interest.

We claim:

1. The new and distinct variety of strawberry plant herein described and illustrated and identified by the characteristics enumerated above.

* * * * *